(12) United States Patent
Ruben

(10) Patent No.: US 6,461,599 B1
(45) Date of Patent: *Oct. 8, 2002

(54) SHAVING COMPOSITION AND METHOD

(76) Inventor: Bradley N. Ruben, 463 First St., #5A, Hoboken, NJ (US) 07030

( * ) Notice: Subject to any disclaimer, the term of this patent is extended or adjusted under 35 U.S.C. 154(b) by 0 days.

This patent is subject to a terminal disclaimer.

(21) Appl. No.: 08/319,131

(22) Filed: Oct. 6, 1994

Related U.S. Application Data

(63) Continuation-in-part of application No. 08/059,781, filed on May 10, 1993, now abandoned.

(51) Int. Cl.⁷ .................................................. A61K 7/15
(52) U.S. Cl. ......................................................... 424/73
(58) Field of Search ........................ 424/73, 401, 70.1; 514/846, 848, 844

(56) References Cited

U.S. PATENT DOCUMENTS

| | | | |
|---|---|---|---|
| 3,903,410 A | * 9/1975 | Akrongold et al. | 424/73 |
| 4,014,995 A | * 3/1977 | Juliano et al. | 424/168 |
| 4,046,874 A | 9/1977 | Gabby et al. | 424/73 |
| 4,240,919 A | * 12/1980 | Chapman | 252/95 |
| 4,440,745 A | * 4/1984 | Schmidt et al. | 424/78 |
| 4,892,727 A | * 1/1990 | Grollier | 424/69 |
| 4,944,939 A | 7/1990 | Moore | 424/73 |

OTHER PUBLICATIONS

*CFTA Cosmetic Ingredient Handbook* (Washington, D.C.: the Cosmetic, Toiletry and Fragrance Assn., 1988).

* cited by examiner

Primary Examiner—James M. Spear

(57) ABSTRACT

A shaving composition for ameliorating pseudofolliculitis barbae contains abrasive particles for aiding in liberation of hairs growing aberrantly. While one method of shaving includes first massaging an abrasive composition on the skin prior to shaving with a water-based shaving lubricant, a preferred method is to use the composite composition, which is first massaged into the skin for its abrasive and hair liberating effects and then the skin is shaved taking advantage of the lubricating nature of the composition. The abrasive particles have a hardness less than that of shaving blade metals and are preferably essentially non-pulverulent.

7 Claims, No Drawings

SHAVING COMPOSITION AND METHOD

This application is a continuation-in-part of application Ser. No. 8/059,781, filed May 10th, 1993, now abandoned, the disclosure of which is incorporated herein by reference.

BACKGROUND OF THE INVENTION

1. The field of the Invention

The present invention generally relates to shaving compositions and methods for their use, especially in the amelioration of pseudofolliculitis barbae.

2. The State of the Art

The art of shaving human skin, and particularly mens' faces, is centuries old. Yet the process for shaving is essentially unchanged. The desired result is a smooth skin surface, but there are many obstacles.

The basic process of drawing a blade across the skin surface assumes that the skin surface is perfectly flat and has an essentially homogeneous surface with respect to such parameters as elasticity, tugor, smoothness, hair type, and the like. Of course, every face possesses unique deviations from this normal, and so the shave may be close or too close in certain areas of the skin and not sufficiently close in others. The art has moved to compensate for these deviations in two general directions. One direction involves the use of improved shaving lubricants which are designed to soften the beard, condition the skin, and otherwise provide an improved shaving environment. Typical lubricants are comprised of water-based foams or foamable gels with soap-like lubricants. The other direction involves manipulating the hair during cutting such that the hair is cut in an extended, taut condition; cutting the hair in such a condition attempts to cut a longer portion of the hair so that the cut hair will reside sufficiently low in the hair follicle that the shave feels close. These manipulations are typically performed by means of a dual razor system (one blade disposed immediately behind and closely with another as in conventional disposable razors; e.g., as sold by Schick or Gillette) or a slidable hair-extending mechanism as is used in certain electric razors (e.g., as sold by Norelco).

In any shaving system, and particularly those which extend the hair prior to cutting, there is a likelihood that the cut hair will reside below the surface of the skin. In this condition, the hair is subject to growing back into the dermis or growing along and just below the surface of the skin rather than back out through the opening of the hair follicle. This abnormal growth can cause infections, skin bumps ("razor bumps" or pseudofolliculitis barbae), and general cosmetic unsightliness, technically referred to as pseudofolliculitis (literally "false follicle" since the hair is growing in a non-existent follicle). The art has considered the use of special brushes for the face prior to shaving to physically open the hair follicles and liberate the ends of the aberrant hairs, and improvements in lubricants to allow the razor blade to perform a similar function safely and/or to further condition the skin and the opening of the follicle. However, there is presently no significant method or formulation for alleviating this condition.

Gabby et al. (U.S. Pat. No. 4,046,874) describes a soapless shaving composition including a polyglycerol ester and an insoluble pulverulent bodying agent to provide the desired texture. The polyglycerol ester is not water soluble and must be foamed in a heated environment (125°–212° F.) A pulverulent is a composition that crumbles (i.e., can be pulverized), and so can be used to provide a more solid feel or body to the foam.

Moore (U.S. Pat. No. 4,944,939) describes a shaving preparation for preventing pseudofolliculitis barbae that includes a glucocorticoid to reduce inflammation and salicylic acid as a keratolytic agent.

SUMMARY OF THE INVENTION

The present invention provides a method for shaving which conditions the skin for the ameliorating pseudofolliculitis barbae by first massaging the face with an abrasive composition and then shaving with a water-based lubricant. A preferred composition is a composite shaving lubricant which includes abrasive particles. The preferred method thus comprises applying the composite composition, massaging the composition into the face, and then shaving with the composition already on the face.

DETAILED DESCRIPTION OF THE INVENTION

The present invention is based on the discovery that the use of an abrasive composition on the face prior to shaving with a water-based lubricant significantly reduces the incidence and severity of pseudofolliculitis barbae.

Abrasive compositions for use in cleansing the skin and face are known in the art; they are especially prevalent in the women's cosmetic market, and some compositions are also available for men's cosmetics and in acne preparations. Such compositions typically include a soap or surfactant designed for cleaning the skin, optional ingredients such as humectants, moisturizers, biocides (e.g., benzoyl peroxide), astringents, and the like, and abrasive particles. These abrasive particles are present to enhance desquamation and generally provide a very light abrasion to the skin. They are composed typically of cellulosic products, such as ground walnut shells, ground apricot kernels, or other plant material (e.g., bark, seed, shell, nut, or combinations thereof), although silica and alumina are also used. One commercially available formulation comprises on its list of ingredients the following: water; finely ground walnut shells; cetyl alcohol; glyceryl stearate; stearic acid; glyceryl stearate and PEG 100 stearate; propylene glycol; octyl hydroxystearate; octyl palmitate; sodium lauryl sulfate; oleyl betaine; sea kelp extract; aloe vera; finely ground apricot kernels; panthenol; allantoin; tetrasodium ethylenediaminetetraacetic acid; apricot kernel oil; sodium PCA; methylparaben; propyleneparaben; fragrance; potassium sorbate; retinyl palmitate (vitamin A); tocopherol acetate (vitamin E); quaternium-15; and coloring. (Available as "Apricot & Sea Kelp Scrub" from Freeman Cosmetic Corporation, Beverly Hills, Calif.) Determining the amount and fineness of the abrasive particles for a particular formulation is within the skill of the ordinary artisan. In fact, because of the variation in skin types, it is preferable that formulations within the scope of this invention be available in different grades of abrasiveness (e.g., very fine, fine, and medium) so that the user can determine which is optimal for his (or her) own use. This commercial composition is described on the labeling as an exfoliant. The surfactants and certain other components of that composition also aid in exfoliation, and it preferable to include such components in the present composition.

The abrasive particles used in this invention are incorporated into a water-based shaving formulation. Such formulations useful in this invention include water-soluble (ionic) surfactants and/or skin lubricants to allow the razor blade to slide across the skin without catching on the skin or hair and penetrating the skin. One typical commercially available pressurized, foamable formulation lists as its ingredients:

water, stearic acid, trietharnolamine, butane, propane, diethylene glycol, dioctanoate/diisononanoate, sodium lauryl sulfate, laureth-23, cetyl alcohol, and fragrance. (Available from Faberge USA, Inc., New York, N.Y., as CUT GUARD Shave Cream.) Another commercially available pressurized, foamable formulation lists as its ingredients: dimethicone (active ingredient); (and as inactive ingredients) water, stearic acid, triethanblamine, propylene glycol, isobutane, palmitic acid, PPG-11 stearyl ether, coconut acid, aloe vera gel, palm oil glyceride, lanolin, propylene glycol dicaprylate/dicaprate, cetyl alcohol, fragrance, sodium metasilicate, trisodium EDTA, propane, and coloring. (Available from Noxell Corporation, Hunt Valley, Md., as Medicated NOXEMA Aloe & Lanolin Shave cream.) A shaving formulation may also be provided in powdered or solid form which must be dissolved in water and brought to a lather.

The inventive method of shaving comprises first massaging a cosmetically suitable abrasive composition on the face (or other skin area to be shaved) and then shaving the face with the assistance of a water-based lubricant. Thus, this invention provides the benefit of a kit which comprises a container/dispenser having an abrasive composition and another container/dispenser having a water-based shaving formulation. The compositions can be packaged separately as the commercially available compositions described above (the scrub in a flexible plastic tube with a screw top, and the shaving cream in conventional pressurized cans with shaving cream spray nozzles for foaming the composition) and then packaged together in a common container for storage.

The novel composition of this invention essentially comprises a conventional water-based shaving formulation with the addition of abrasive particles. The composition may also include ingredients such as stearic acid, sodium lauryl sulfate, EDTA, and the like to aid in desquamation and exfoliation, as well as other conventionally added ingredients as in the compositions noted above. As mentioned, the amount and fineness of the abrasive particles used will vary depending upon the abrasive effect desired, and will vary among people because of their differing skin types and facial structures.

The abrasive particles should have a hardness which is less than that of steel and like compositions used for shaving blades, but which is sufficient to provide a safe abrading effect on the skin. Accordingly, preferred abrasive particle compositions are cellulosic, such as ground shells, ground kernels, coarse flours and meals, brans, and the like, and mixtures thereof, derived from cereals and other grains, nuts and legumes, fruit seeds and pits, wood and/or bark from trees and shrubs, and mixtures thereof; for example, willow bark may provide both abrasive and keratolytic effects. Various cosmetic abrasives can be found in *CFTA Cosmetic Ingredient Handbook* (Washington: The Cosmetic, Toiletry, and Fragrance Assn., 1988), including such relatively soft materials as chalk and corn starch. Additionally, hard plastics can also be suitable, and especially thermoplastics since such cannot readily be recycled.

Although relatively soft materials like talc may be considered abrasives if rubbed on the skin for a long time, corn starch (usually with tricalcium phosphate, also conventionally considered an abrasive) is often sold as baby powder and so is not sufficiently abrasive to be useful in the present invention. On the Mohs hardness scale, talc has a value of 1 while steel has values ranging from about 5 to 8.5; accordingly, abrasive particles useful in this invention should typically have a hardness in the range of about 2 to about 4. Nevertheless, the function of the abrasive particles in this invention is to abrade the skin sufficiently to liberate the hairs that are not free and/or extending above the skin line. As such, various pulverulent compositions, ranging in hardness from talc to alumina, are not suitable for the present invention because of their ability to crumble. Although a pulverulent may function as an abrasive effective to liberate ingrown hairs if rubbed on the skin for a sufficiently long period of time, in practical terms a consumer will not be likely to use a product requiring an application period of more than one minute,, and more typically will consider 15 seconds to be a tolerable period for rubbing or massaging the composition of this invention on the area to be shaved. The abrasive particles of the present invention are those which are essentially not pulverulent and can, in effect, remain their integrity while (essentially) opening the skin directly above an ingrown hair, helped by the raised surface of the skin due to the underlying hair. Thus, while some pulverulence may be tolerated, when rubbed on the skin the abrasive particles should be essentially non-pulverulent so that when they are forced into (or onto) a "razor bump" they are not pulverized but instead abrade the skin. Ceramic and mineral abrasives can also be used, although increased wearing of the shaving blade may occur, the additional cost of replacement blades is significantly outweighed by the increased skin comfort and the perceived benefit in cosmetic appearance.

When used with a conventional pressurized, foamable composition, the valving and conduits for the effluent shaving cream must be sized to accommodate the size of the abrasive particles. Although the abrasive particles may cause wear in the dispensing device, such devices are typically designed not to be refilled and reused.

After having grown a beard for approximately six months, the inventor hereof shaved the beard and began to shave regularly using the aforementioned CUT GUARD shaving cream and using either a BIC Sensitive Skin razor (BIC Corporation, Milford, Conn.) or a PANASONIC model ES868 wet/dry razor (Matsushita Electric Co., Ltd., Tokyo, Japan). Within two weeks pseudofolliculitis barbae had developed and continued unabated for approximately one month. Thereafter, approximately 1.5 $cm^3$ of the aforementioned Apricot & Sea Kelp Scrub was massaged on the skin with the addition of a few drops of water prior to shaving each day. Within two weeks, the severity of the pseudofolliculitis barbae was dramatically reduced and was essentially alleviated. Compositions were also prepared by hand mixing approximately 1.5 $cm^3$ of the Scrub and about 40–45 $cm^3$ of the shaving cream, massaging this composite composition on the skin, and then shaving as normal, with both the straight/disposable razor and the electric razor. Close shaves with no reoccurrence of pseudofolliculitis barbae were achieved.

The composition and method of this invention, although not desirous of being constrained to a particular theory, are believed to alleviate pseudofolliculitis barbae most effectively when used on a continuing basis. The continual use provides a constant abrasion to the skin to quickly reach aberrantly growing hairs, and to promote the removal of dead skin cells and skin newly grown lying over hairs on the skin surface. Initial use of the composition may result in apparent increased irritation because of the irritated, sensitive, and/or uneven nature of the skin due to the presence of pseudofolliculitis barbae. Continued use of the composition via the method of this invention dramatically reduces the occurrence of pseudofolliculitis barbae and thus accompanying the irritation and sensitivity.

Additional ingredients can include those conventionally used in cosmetics, such as bodying agents, colorants, fragrances, emollients, demulcents, and the like. Further optional ingredients include medications to combat inflammation and/or infection (e.g., a glucocorticoid, benzoyl peroxide). Still further, a keratolytic agent, such as salicylic acid in the approximate amount of 1–5%, is also desirable, and is preferred for compositions that can be left on the skin for longer periods of time (e.g., with the aid of a humectant).

The invention having been described to enable one of ordinary skill in the art, such an artisan may derive modifications or additions thereto which are intended to be within the scope and spirit of the invention as defined by the following claims.

What is claimed is:

1. A method of shaving human skin with a blade which comprises: first rubbing a cosmetically suitable composition including an effective amount of essentially non-pulverulent abrasive on an area to be shaved by a blade, said rubbing conducted for a time effective for the particles to abrade the skin, said particles having a hardness less than that of said blade; applying a water-based shaving lubricant comprising a water-soluble soap or ionic surfactant to the area; and shaving the area.

2. The method as defined by claim 1, wherein the abrasive composition and the shaving lubricant are applied simultaneously as a composite composition, rubbing the composite composition, and then shaving.

3. A shaving kit which comprises a container/dispenser comprising (i) a cosmetically suitable composition comprising essentially non-pulverulent abrasive particles having a hardness less than that of shaving blade metals and (ii) a container/dispenser comprising a water-based shaving lubricant including a water-soluble soap or surfactant, the containers being housed together in common packaging.

4. A shaving cream composition for the preparation and shaving of skin to be shaved by applying and rubbing said composition onto said skin, which composition comprises: a water-based shaving lubricant and a water-soluble soap or ionic surfactant; and essentially non-pulverulent, cosmetically-suitable abrasive particles having a hardness less than that of shaving blade metals, wherein said particles are selected from the group consisting of ground shells, ground kernels, coarse flours and meals, brans, and mixtures thereof, derived from cereal grains, nuts and legumes, fruit seeds and pits, wood and/or bark from trees and shrubs, and mixtures thereof.

5. The composition as defined by claim 4, wherein said particles are comprised of ground walnut shells, ground apricot kernels, or a mixture thereof.

6. The composition as defined by claim 5, wherein the composition is provided in a pressurized container for foaming.

7. The composition as defined by claim 5, further comprising a keratolytic agent.

* * * * *

UNITED STATES PATENT AND TRADEMARK OFFICE
CERTIFICATE OF CORRECTION

PATENT NO. : 6,461,599 B1
DATED : October 8, 2002
INVENTOR(S) : Bradley N. Ruben It is certified that error appears in the above-identified patent and that said Letters Patent is hereby corrected as shown below:

Column 3,
Line 57, delete "cannot" and replace with -- can --.

Signed and Sealed this

Twelfth Day of April, 2005

JON W. DUDAS
*Director of the United States Patent and Trademark Office*